United States Patent

Busby

(10) Patent No.: US 9,352,154 B2
(45) Date of Patent: May 31, 2016

(54) INPUT SELECTION FOR AN AUDITORY PROSTHESIS

(75) Inventor: Peter Busby, Caulfield (AU)

(73) Assignee: Cochlear Limited, Macquarie University, NSW (AU)

( * ) Notice: Subject to any disclaimer, the term of this patent is extended or adjusted under 35 U.S.C. 154(b) by 529 days.

(21) Appl. No.: 13/013,615

(22) Filed: Jan. 25, 2011

(65) Prior Publication Data

US 2011/0125218 A1  May 26, 2011

Related U.S. Application Data

(63) Continuation-in-part of application No. 12/532,633, filed as application No. PCT/AU2008/000415 on Mar. 25, 2008, now abandoned.

(30) Foreign Application Priority Data

Mar. 22, 2007 (AU) ................ 2007901517

(51) Int. Cl.
*A61N 1/36* (2006.01)
(52) U.S. Cl.
CPC .................. *A61N 1/36032* (2013.01)
(58) Field of Classification Search
CPC .............. A61N 1/36032; A61N 1/0541
USPC ...................................... 607/55, 57
See application file for complete search history.

(56) References Cited

U.S. PATENT DOCUMENTS

| | | | |
|---|---|---|---|
| 6,151,400 A | | 11/2000 | Seligman |
| 2004/0172242 A1* | | 9/2004 | Seligman et al. ............. 704/225 |
| 2004/0252852 A1 | | 12/2004 | Taenzer |
| 2005/0107843 A1* | | 5/2005 | McDermott et al. ............ 607/57 |
| 2006/0235490 A1 | | 10/2006 | Killian et al. |
| 2006/0247735 A1 | | 11/2006 | Honert |
| 2007/0016267 A1 | | 1/2007 | Griffin et al. |

FOREIGN PATENT DOCUMENTS

| | | |
|---|---|---|
| AU | 2004200790 | 9/2004 |
| EP | 1018854 | 7/2000 |
| WO | WO 9826629 | 6/1998 |
| WO | WO 9941938 | 8/1998 |
| WO | WO-02096153 | 11/2002 |
| WO | WO 2007028250 | 3/2007 |

OTHER PUBLICATIONS

International Search Report issued in PCT/AU2008/000415, mailed May 29, 2009.

* cited by examiner

*Primary Examiner* — Tammie K Heller

(57) ABSTRACT

Providing stimulation signals for an implanted auditory prosthesis including receiving first and second sound signals at first and second sound input devices, each of the first and second signals having a signal-to-noise ratio; determining a signal parameter related to said signal-to-noise ratio of each of the first and second signals; selecting one of the first and second signals which has the greater signal-to-noise ratio; and generating stimulation signals for the implanted auditory prosthesis based on said selected sound signal.

16 Claims, 5 Drawing Sheets

INPUT SELECTION FOR AN AUDITORY PROSTHESIS

CROSS-REFERENCE TO RELATED APPLICATIONS

This application is a Continuation-in-Part of U.S. patent application Ser. No. 12/532,633, entitled "Bilateral Input Selection for Auditory Prosthesis," having a filing/371(c) date of Apr. 26, 2010, now abandoned, which is a national stage application under 35 USC §371 (c) of PCT Application No. PCT/AU2008/00415, entitled "Bilateral Input For Auditory Prostheses," filed on Mar. 25, 2008, which claims priority from Australian Patent Application No. 2007901517, filed on Mar. 22, 2007. The entire disclosure and contents of the above applications are hereby incorporated by reference herein.

BACKGROUND

1. Field of the Invention

The present invention relates generally to auditory prostheses, and more particularly, selecting audio signals for auditory prostheses.

2. Related Art

Auditory prostheses are provided to assist or replace the perception of hearing for affected individuals. Such devices include cochlear implants, middle ear implants, brain stem implants, implanted mechanical stimulators, electro-acoustic devices, and other devices which provide electrical stimulation, mechanical stimulation, or both.

In the everyday sound environment, the auditory prosthesis recipient listens to a target sound, typically speech, in the presence of background noise. In most environments, the locations of the target sound and noise sources are not the same. For example, source of speech is often in front of the auditory prosthesis recipient as the recipient is usually looking at the person talking. On the other hand, the source(s) of noise are often on the side or other locations relative to the recipient when the recipient is facing the speaker.

Background noise interferes with speech understanding, and if the level of noise approaches that of the target signal, the auditory prosthesis recipient is unable to effectively distinguish the target sound from the noise. The signal-to-noise ratio (SNR) is one measure of this influence of noise upon the target sound signal; a high SNR implies relatively low noise while a low SNR implies a relatively high noise level.

SUMMARY

In accordance with one aspect of the invention, there is provided a method for generating stimulation signals in an implanted auditory prosthesis, comprising: receiving first and second sound signals at first and second sound input devices; determining a signal parameter for each of the first and second signals, wherein the parameter represents a noise floor of each of the first and second sound signals; determining a signal based on the first and second sound signals and the determined signal parameters; and generating stimulation signals using said determined signal to cause a hearing percept.

In accordance with another aspect of the invention, there is provided a auditory prosthesis comprising: a first sound input device configured to receive a first sound signal; a second sound input device configured to receive a second sound signal; and at least one processor configured to determine a signal parameter for each of the first and second sound signals representing a noise floor of each of the first and second sound signals; determine a signal based on the first and second sound signals and the determined signal parameters; and generate stimulation signals based on the determined signal.

In accordance with yet another aspect of the invention, there is provided a auditory prosthesis, comprising: a first sound input means for receiving a first sound signal; a second sound input means for receiving a second sound signal; means for determining a parameter for each of the first and second sound signals, where the parameters represents a noise floor of each of the first and second sound signals; means for determining a signal based on the first and second sound signals and the determined parameters; and means for generating stimulation signals based on said determined signal.

BRIEF DESCRIPTION OF THE DRAWINGS

Illustrative embodiments of the present invention are described herein with reference to the accompanying figures, in which.

DETAILED DESCRIPTION

Broadly, aspects of the present invention provide an arrangement in which sound signals associated with both ears are received. A signal from one of the two sides is selected (e.g., the signal having the highest quality) as the basis for stimulation. The parameter used for selecting which received sound signal to use may be determined, for example, at one or both of devices fit to each ear of the recipient, or at some other part of the system such as a separate component.

In embodiments, the parameter used for selecting the signal may be any parameter indicative of the quality of a signal. For example, the parameter may be the signal to noise ratio (SNR) or an estimate of the SNR, where the signal with the highest SNR is used as the basis for stimulation. In another embodiment, the noise in each signal is measured to obtain a noise floor indicative of the lowest noise level in the signal over a period of time. This noise floor measurement provides an assessment of the quality of the signal that may then be used for selecting the signal to be used for application of stimulation. It should be noted that these are but some examples of parameters for assessing the quality of a signal and in other embodiments other parameters may be used.

Embodiments of the present invention are described herein primarily in connection with one type of auditory prosthesis (also sometimes referred to as an "hearing prosthesis"), namely a cochlear prostheses (commonly referred to as a cochlear prosthetic devices, cochlear implant, cochlear devices, and the like; simply "cochlear implant" herein.)

Cochlear implants generally refer to auditory prostheses that deliver electrical stimulation to the cochlea of a recipient. As used herein, cochlear implants also include auditory prostheses that deliver electrical stimulation in combination with other types of stimulation, such as acoustic or mechanical stimulation. It would be appreciated that embodiments of the present invention may be implemented in any cochlear implant or other auditory prosthesis now known or later developed including auditory brain stimulators (also referred to as brain stem implants), or implantable auditory prostheses that acoustically or mechanically stimulate components of the recipient's middle or inner ear, or any combination of such devices. The devices may have an external processor, or may be partially implanted, with only an external microphone, or even completely implanted including the microphone or other sound transducer.

Figure 1:
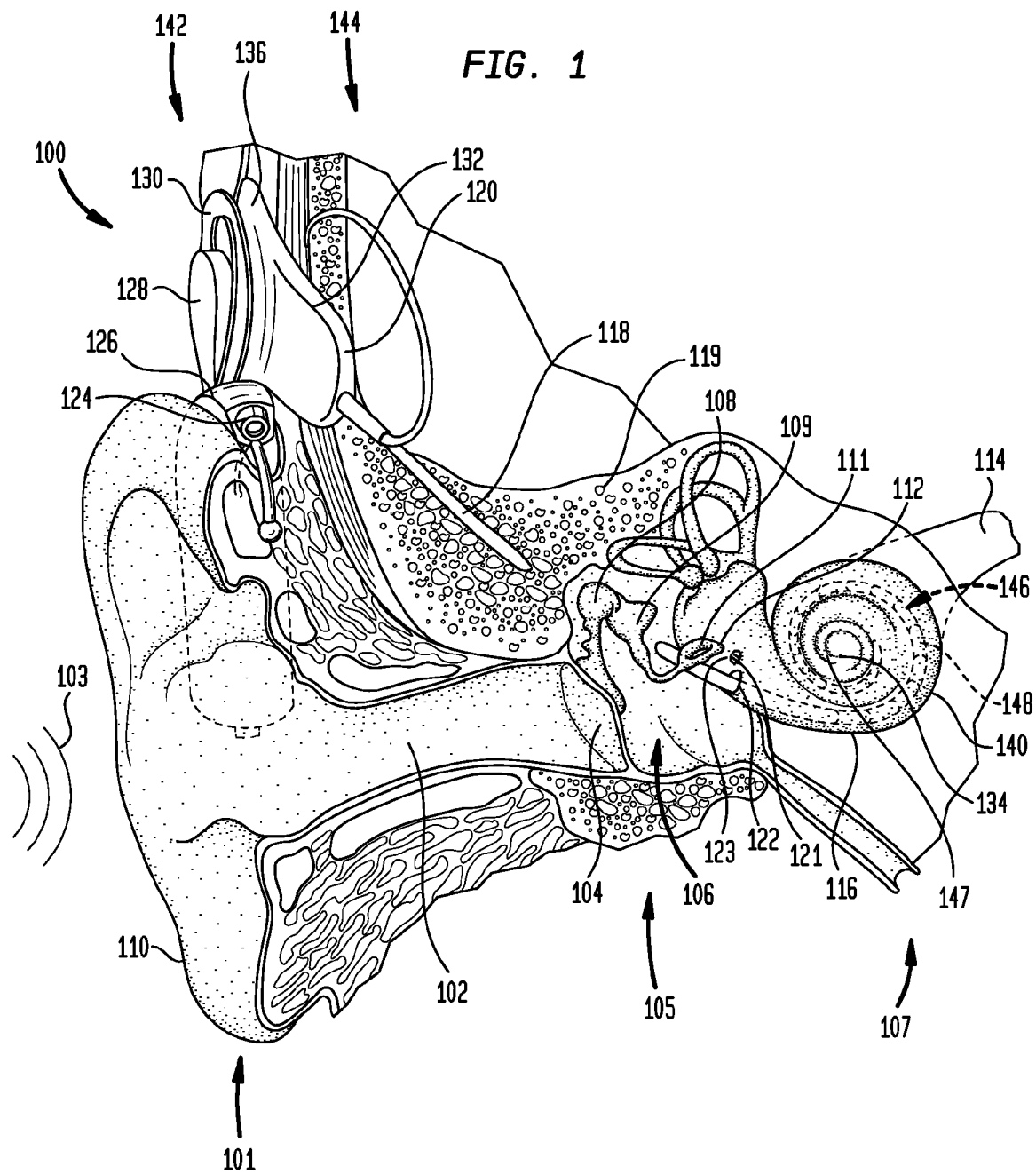
FIG. 1 is a perspective view of a cochlear implant in which embodiments of the present invention may be implemented.

FIG. 1 is perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100. Although FIG. 1, only illustrates a single cochlear implant 100, it should be understood that the cochlear implant system may comprise a cochlear implant 100 fitted to both ears of the recipient. Systems in which a auditory prosthesis (e.g., a cochlear implant) are fitted to both of a recipient's ears are referred to as bilateral systems, and systems in which only one auditory prosthesis is used are referred to as unilateral systems.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input devices, such as microphone 124 for detecting sound, a sound processing unit 126 (also referred to herein as sound processor 126) or a jack for receiving a sound signal from another device, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown). In an embodiment, microphone 124, sound processing unit 126, and the power source may be included in a single housing. This housing may be configured to fit behind the ear of the device, and is referred to herein as a Behind-the-Ear (BTE) device. It should be understood, however, that these components may be housed separately or in a differently configured housing.

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119, and is implanted into cochlea 104. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

The sound processing unit 126 may store a set of parameters that the sound processing unit 126 uses in processing sound to generate the encoded signals specifying the stimulation signals to be applied by electrodes 148. This set of parameters and their respective values is collectively and generally referred to herein as a "parameter map," a "cochlear map" or "MAP." A "MAP" is also sometimes referred to as a "program."

When a recipient first receives a cochlear implant 100, the system 100 is fitted or adjusted to the recipient since each recipient experiences different sound perceptions. It is noted that fitting may also be periodically performed during the operational use of the cochlear implant system 100. As used herein the terms "fit," "adjust," "program," "fitting," "adjusting," "mapping," or "programming," relate to determining one or more device parameters for a device. These device parameters may include parameters resulting in electronic or software programming changes to the stimulating medical device. The particular device parameters determined during the fitting session may vary depending on the multimodal hearing system. In the cochlear implant of FIG. 1, the device parameters may include one or more of the MAP parameters. These MAP parameters may include, for example, the number of channels, T-levels, C-levels, gain, frequency of stimulation, compression characteristic, type of strategy, number of maxima, etc.

Figure 2:
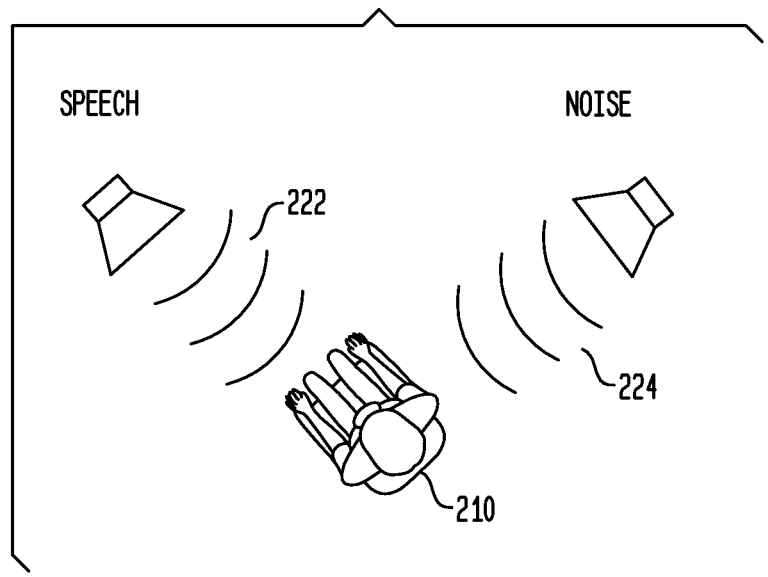
FIG. 2 is an environment in which there is a target speech signal and noise.

FIG. 2 shows a typical sound environment that an auditory prosthesis recipient may encounter. The user 210 is shown seated on a chair. There is a signal that user 210 desires to hear, referred to as target signal 222. Typically, target signal 222 is a speech signal. Also illustrated is a source that generates noise signal 224. This noise signal may be any type of noise signal, such as background noise, highway noise, etc.

In the environment of FIG. 2, the user 210 is fitted with either a unilateral or bilateral cochlear implant system. In the unilateral system, the cochlear implant system may comprise a BTE device fitted to either the right or left ear of the user 210, and in a bilateral system, a BTE is fitted to both ears. On average, the probability of noise being from the right or left side of the recipient is equal in the everyday listening environment. In a unilateral system, when noise is from the same side as the microphone (e.g., included in the BTE), the signal-to-noise ratio will be worse than if noise was from the opposite ear side. This phenomenon is known as the headshadow effect, which is essentially the attenuation of noise by the head. Bilaterally implanted users take advantage of this effect by consciously listening to the ear with the better signal-to-noise ratio, similar to a person with normal hearing. However, as described below, the embodiments of the present invention may have advantages for a bilaterally implanted recipient as well.

To take advantage of this headshadow effect, according to one implementation, the auditory prosthesis recipient wears two speech processors, with one processor situated at each ear. The two processors may be connected by cable for communication, or alternatively by radio frequency or other wireless communication method not requiring direct cable connection.

Figure 3:
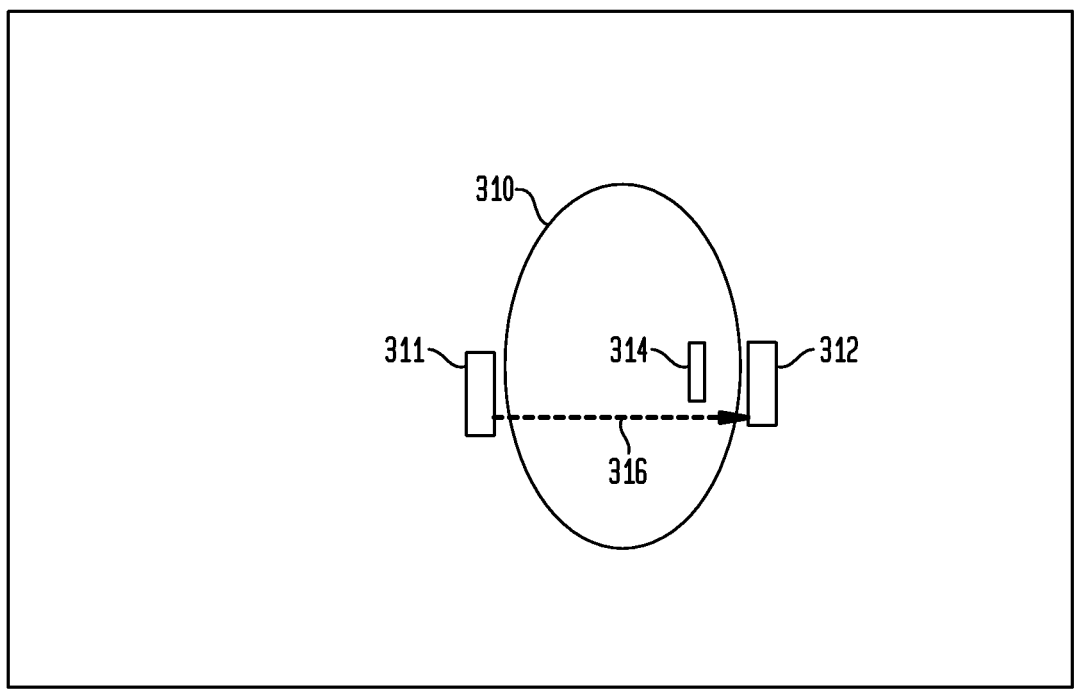
FIG. 3 is a schematic view of a recipient wearing a processor on each ear, in accordance with an embodiment of the present invention.

FIG. 3 illustrates an exemplary auditory prosthesis arrangement, in accordance with an embodiment of the present invention. As illustrated, an implanted device 314 has been implanted in a user 310. This implanted device 314 may be, for example, an internal component of a cochlear implant such as discussed above with reference to FIG. 1. As shown, a processor 312 is provided on the same side as the implanted device 314, which for convenience is referred to herein as the A side. Processor 312 may be a sound processor, such as sound processor 126 of FIG. 1 and included in a BTE such as discussed above.

A processor 311 is also provided on the contralateral side, which we will refer to hereafter as the B side. Processor 311 may be identical to or a simplified version of sound processor 126 and may similarly be included in a BTE device that also includes one or more microphones. Or, for example, processor 311 may be a relatively simple device, having a microphone and a transmission arrangement to send raw audio data to the processor 312, or at a level of complexity and processing power in between. The two processors 311 and 312 are connected by a suitable communications link 316, for example a cable or a wireless communications link, such as Bluetooth.

As will be described in more detail below, in this arrangement, processor 312 determines whether the sound signal received on either the A or B side has the best signal-to-noise ratio. The output of that processor is then used as the basis for stimulation. It will be appreciated that the signal-to-noise ratio is only one particular measure which is used in the present implementation, and that embodiments of the present invention can be implemented using many alternative measured or calculated parameters that are representative or indicative of the quality of the received sound signal.

In another embodiment, there may be a single speech processor and two microphones, with one microphone associated with each ear. In such an embodiment, the speech processor would process the signals from each of the microphones. It is should be noted that although the present embodiment is discussed with reference to the presence of a microphone or other transducer associated with each side of the user's head, in embodiments any suitable arrangement of processors and microphones may be used. For example, the microphones or other sound transducers may be external, partially or totally implanted, totally or partially in the ear canal, and associated with processors or not.

In a simple implementation, the B side may be a simple microphone, connected by a cable to a speech processor on the A side. Or, in an embodiment, the processor selecting which sound signal to use for stimulation could be separate from each of the microphone/processor devices fitted to each ear. For example, in a cochlear implant which is partially or fully implanted, each ear may be fitted with a simple microphone device or other device that provides data (e.g., either the raw sound data, the stimulation signals, or something in between) to the implanted component of the cochlear implant, which determines which of the received signals is of better quality (e.g., has a higher SNR).

Embodiments of the present invention may also be applied to a bilaterally implanted user. In this case, the selection of which signal to use can be performed by one of the speech processors, or the operations may be shared among the speech processors.

The required bandwidth and data rate for transmitting the signal between the two processors 311 and 312 over communication link 316 depends on what data is being transmitted and the complexity of the device being used. For example, if the raw audio signal as picked up by the B side microphone is transmitted to the A side, the bandwidth will have to be large enough to cover the approximately 8 kHz of the typical cochlear implant audio frequency range at a high enough data rate. The data rate needs to be high enough to ensure that the signals from each processor are very close to being synchronized when received by the A side processor. If the delay between the signals is too large, then if the B side has the signal with the higher SNR, when the prosthesis processor on side A comes to process the transmitted signal, the speech percepts heard by the recipient will not be synchronized with the speaker's lip movements.

The signal sent from the B side may be subjected to varying levels of pre-processing. At one extreme is the transmission of raw audio data; at the other may be a fully formed set of stimulation instruction for the prosthesis. The data transmitted may be at any suitable intermediate level.

An audio compression algorithm could be used to reduce the required bandwidth. For example, US 2006/0235490 assigned to the present applicant, the disclosure of which is hereby incorporated by reference herein, discloses a suitable coding strategy which could be applied. Other suitable commercial audio compression algorithms could also be used.

Referring back to FIG. 3, in an embodiment, each processor 311 and 312 independently measures the signal-to-noise ratio of the sound signal received by the processor 311 and 312, respectively, using a suitable algorithm, for example an automatic sensitivity control (ASC) algorithm. The ASC algorithm automatically adjusts the gain of the initial amplifier in the signal pathway, according to the level of background noise.

Figure 4:
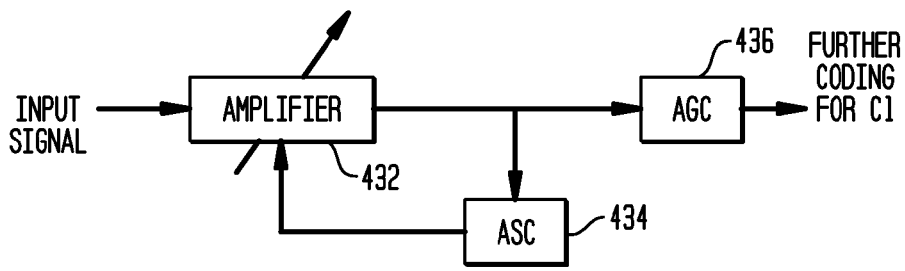
FIG. 4 is a block diagram of an automatic sensitivity control arrangement.

FIG. 4 illustrates a prior art ASC arrangement, for example as described in relation to a regular, unilateral arrangement in U.S. Pat. No. 6,151,400, the disclosure of which is hereby incorporated by reference. In this arrangement, the output of the (initial) amplifier 432 is used as an input to the ASC 434. The output of the initial amplifier 432 is the input for the automatic gain control (AGC) amplifier 436. Parameters in the ASC 434 monitor the noise floor, and have pre-set breakpoint level and timing parameters. This allows the gain to be adjusted in response to the ambient noise, and hence in response to the SNR. The perceptual effect of the ASC 434 is a reduction in the loudness of background noise.

Figure 5:
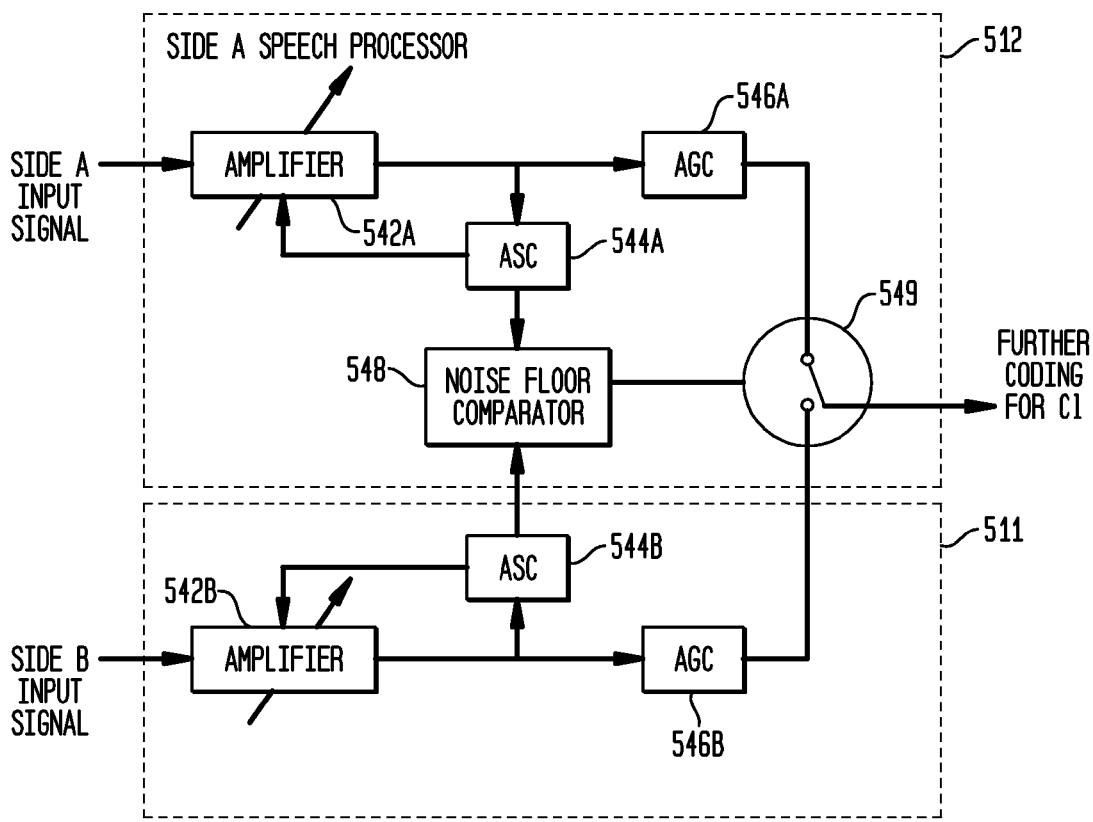
FIG. 5 is a block diagram of processors for each side of a recipient, in accordance with an embodiment of the present invention.

This arrangement of FIG. 4 can be applied to the A and B side signals of the system of FIG. 3. For example, FIG. 5 illustrates an exemplary A side speech processor 512 and a B side processor 511. As shown, speech processor 512 comprises an amplifier 542A, an AGC 546A, an ASC 544A, a noise floor comparator 548, and a switch 549. Processor 511 comprises an amplifier 542B, an ASC 544B, and an AGC 546B. In this implementation, for both the A and B side, the respective audio input signal is processed by initial amplifier 542A, 542B, respectively, the output of which forms the input to the respective AGC 546A, 546B. Each ASC 444A, 444B also receives the amplifier 542A and 542B, respectively, output, and feeds back a control signal to the amplifier 542A and 542B, respectively. Further, according to the present implementation, as noted, a noise floor comparator 548 is provided on the A side. Each ASC 544A, 544B outputs a measure of the noise floor on its respective side to the noise floor comparator 548. For example, as noted above, the B side processor 511 may communicate with the A side processor 512 via a communications link, such as communications link 516 of FIG. 3. In this implementation, the characteristics of the ASCs 544A, 544B are the same.

Comparator 548 outputs the difference between the side A and side B noise floor values. The value output from the comparator 548 is used to control switch 549. In this implementation, when the comparator 548 output value is less than or equal to a threshold value, comparator 548 directs switch 549 to deliver the signal from side A to the implant. When the output value from the comparator 548 is above the threshold, comparator 548 directs switch 549 to deliver the signal from side B. The threshold value of the comparator 548 can be set as appropriate. The default condition in this implementation may be to present side A.

The noise floor comparator 548 may have an adjustable time constant, typically in the order of seconds. The background noise level from each ASC 544A, 544B may be averaged over a time period, and this averaged value is what is provided to the comparator 548. This ensures that the signal delivered to the user is not constantly changing from side to side, which could be distracting for the user. It is preferred that relatively slow time constants are used, so that that the selection program function does not switch quickly across the two processors which could be confusing for the auditory prosthesis recipient.

Figure 6:
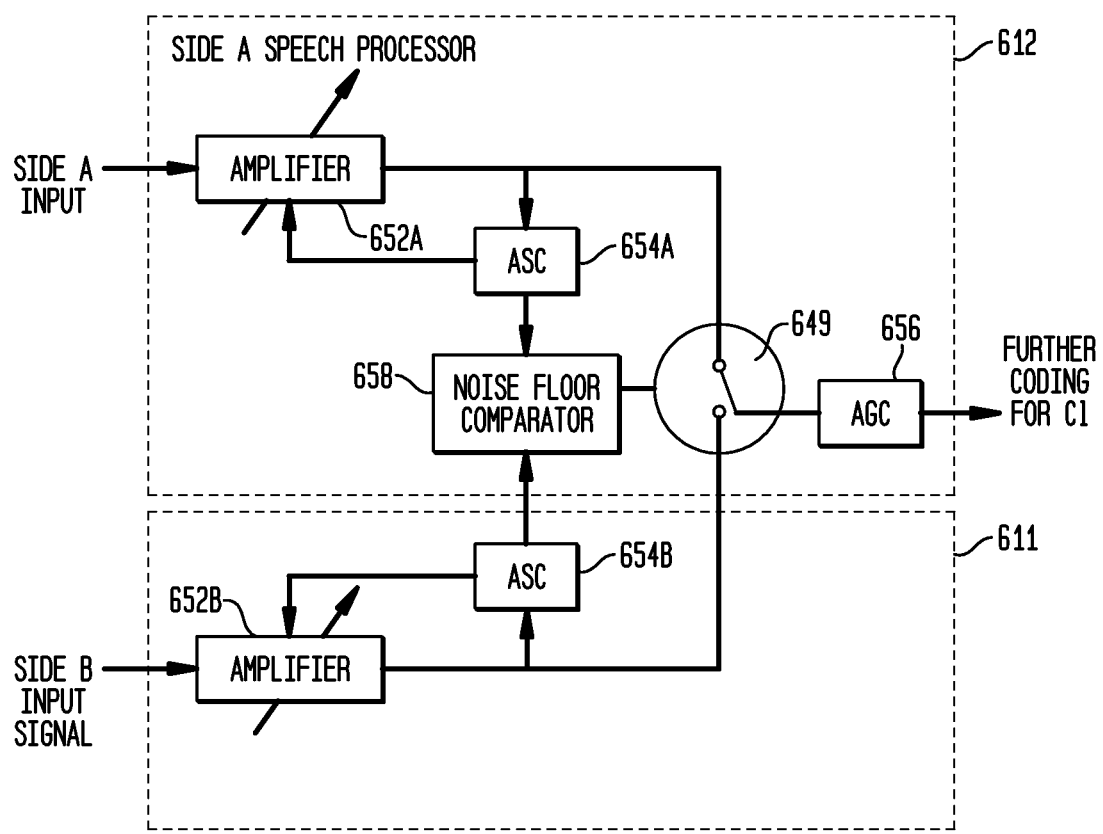
FIG. 6 is a block diagram showing an alternative implementation of processors for each side of a recipient, in accordance with an embodiment of the present invention.

An alternative arrangement is illustrated in FIG. 6. In this arrangement, instead of each side having an AGC, the processor 611 on the B side and the processor 612 on the A side share an AGC 656. In this implementation, the processor 611 on the B side could be a simpler device, such as a headset microphone, including an amplifier 652B and ASC function 654B. The speech processor 612 on the A side in this implementation performs a noise floor comparison 658, and outputs the selected signal to a shared AGC 656. In all other aspects, the processors 611 and 612 may operate in a similar manner to processors 511 and 512, respectively, of FIG. 5.

In the above-discussed implementations, the A side processor according to the implementations described has the additional function of receiving from both processors the measured signal-to-noise ratio. In an alternative implementation involving an implanted device, the measured SNR (or other measure of the quality of the signal) could be provided from external processors to the implanted component which then compares the signal and determines which signal to used. Or, in yet other implementations, this comparison may be performed by some other component.

Figure 7:
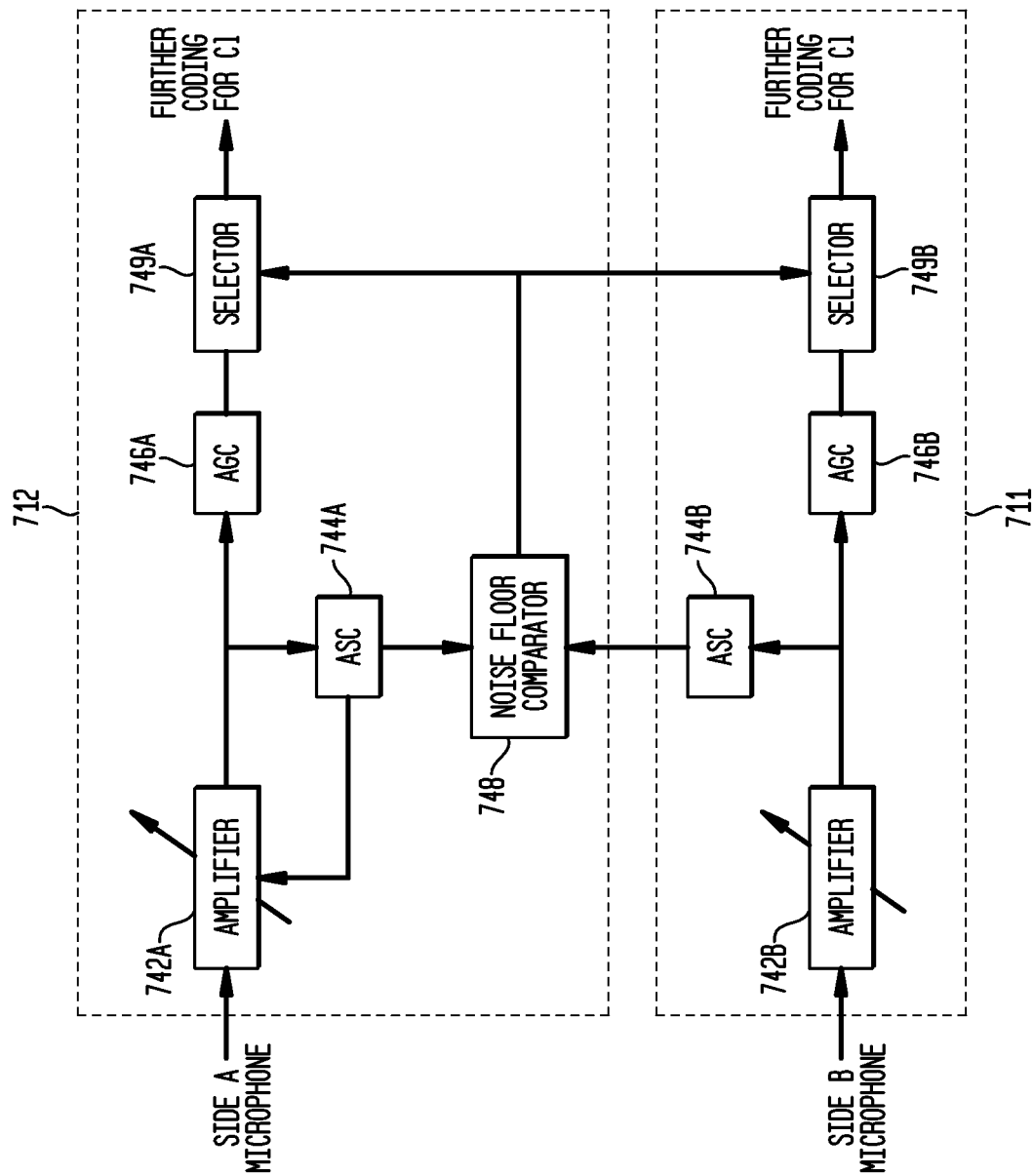
FIG. 7 is a block diagram showing an implementation of a bilateral system, in accordance with an embodiment of the present invention.

Although the above discussed embodiments of FIGS. 3, 5 and 6 were discussed with reference to the cochlear implant system being a unilateral system, as noted above, similar systems could be implemented in a bilateral system. FIG. 7 illustrates an exemplary binaural system, in accordance with an embodiment. As illustrated, the system comprises an exemplary A side speech processor 712 and a B side speech processor 711. As shown, speech processor 712 comprises an amplifier 742A, an AGC 746A, an ASC 744A, a noise floor comparator 748, and a selector 749A. Speech processor 711 comprises an amplifier 742B, an ASC 744B, an AGC 746B, and a selector 749B. The amplifiers, AGCs, and ASCs for the A and B side processors 712 and 711, respectively, may operate in a similar manner to the similarly named components of FIG. 5.

In operation, the ASCs 744A and 744B provide a measure of the quality (e.g., signal to noise ratio) of the A and B side input signals, respectively, to the noise comparator 748. Although, in the illustrated embodiment, the noise comparator 748 is included in the A side speech processor 712, it should be noted that in other embodiments, the comparator 748 may be included in the B side processor 711, the functionality may be shared between the A and B side processors, or the comparator may be included in some other device (e.g., in an implanted component).

The output from the noise floor comparator 748 may be provided to the selectors 749A and 749B in the A and B side processors 712 and 711, respectively. If the output from the noise comparator 748 is less than or equal to a threshold, the A side selector 749A transfers the sound signal from AGC 746A to the components of the speech processor 712 for generating stimulation to be applied to the recipient. If the output from the noise comparator is above the threshold, selector 749A transfers a null signal so that stimulation is not applied by the A side speech processor 712. Or, for example, if the output of the noise comparator is above the threshold, selector 749A may attenuate (e.g., reduce the gain of AGC 746A) the sound signal and transfer the attenuated sound signal to the components of speech processor 724 for generating stimulation.

Similarly, if the output from the noise comparator 748 is greater than the threshold, the B side selector 749B transfers the sound signal from AGC 746B to the components of the speech processor 711 for generating stimulation to be applied to the recipient. If the output from the noise comparator 748 is less than or equal to the threshold, selector 749B transfers a null signal so that stimulation is not applied by the B side speech processor 711. Or, for example, if the output of the noise comparator is less than or equal to the threshold, selector 749B may attenuate (e.g., reduce the gain of AGC 746B) the sound signal and transfer the attenuated sound signal to the components of speech processor 711 for generating stimulation. It should be noted that this is but one example of a mechanism for selecting a sound signal for application of stimulation in a bilateral system, and in other embodiments other mechanisms may be used.

Although the above described embodiments were discussed with reference to both the A and B sides using standard microphones. In other embodiments, the microphones may be directional microphones, such as a beamforming microphone (also referred to as a microphone array).

Further, in embodiments, one or more of the microphones may output a plurality of sound signals representative of sound arriving from different directions. For example, in an embodiment, one or more of the microphones be a multibeam antenna with one beam pointed towards the front of the recipient, one pointed perpendicular to the recipient's ear, and one beam pointed towards the rear of the recipient. In such an embodiment, the noise comparator may receive a measure of the quality of the signal (e.g., the SNR for the signal) received for each beam, and then the comparator may select to apply stimulation using the received signal having the highest measured quality (e.g., SNR).

In the above-discussed embodiment of FIGS. 5 and 6, the sound signals from the A and B sides were compared by measuring their respective noise floors. As noted above, the noise floor is but one example of a measure that may be used for assessing the quality of the signals on the A and B side. For example, in other implementations other measures or mechanisms may be used. For example, in an embodiment, signal to noise ratio estimation techniques may be used to obtain a measure of the quality of the signal. Or, for example, in embodiments, the A and B side processors may include a component (e.g., software component) for measuring the SNR of the respective input signal. The measured SNR may then be provided to a comparator that compares the received SNR values and outputs a signal specifying which of the input signals should be used for application of stimulation. A switch or other selector device(s) may then select and output the specified signal. This output signal may then be used to apply stimulation to the recipient.

As noted above, once the appropriate signal is selected, stimulation is applied by the device to the recipient in accordance with the selected signal. The nature of the signal output by the speech processor will vary with the type of device. For a cochlear implant device, the signal output from the speech processor may be detailed electrode and amplitude data. For example, referring back to the embodiments of FIG. 5 the signal output from the comparator 549 may be used by provided to components (e.g., software, hardware, and or a combination of same) of the speech processor 512 that generate detailed electrode and amplitude data for the application of stimulation. Or, in another embodiment, the speech processor 512 may provide the data from the AGCs 546A or 546B to an implanted component which determines the electrode and amplitude data for the generation of stimulation.

For an implanted mechanical stimulation device, the speech processor may provide the raw or a modified version of the selected signal to the implanted component, which then applies mechanical stimulation to the recipient in accordance with the received signal. Or, for example, the speech processor may use the selected signal to generate instruction data that is provided to the internal component and specifies how the internal component is to apply the stimulation.

For an electroacoustic device, the speech processor may use the selected signal to generate electrode and amplitude data for the electrical stimulation as well as an audio signal for the acoustic stimulation. The speech processor may then provide this electrical stimulation data and audio signal to the respective devices (e.g., a cochlear implant and loudspeaker, respectively) for applying the electrical and acoustic stimulation.

Various implementations of the subject matter described, such as the embodiments of FIGS. 3, 5, 6, and 7 may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. For example, whilst the present invention is described with reference to two microphones, it will be appreciated that the principal could be applied to a larger number of microphones, or to signals which are derived from microphone arrays.

What is claimed is:

1. A method for generating stimulation signals in an auditory prosthesis system comprising:
receiving a first sound signal at a first sound input device;
receiving a second sound signal at a second sound input device;
determining a first noise floor indicative of a lowest noise level in the first sound signal;
determining a second noise floor indicative of a lowest noise level in the second sound signal;

comparing the first noise floor to the second noise floor to select a sound signal from one of the first sound signal or the second sound signal that has the lowest noise level; and based on at least the selected sound signal, generating stimulation signals capable of causing a hearing percept.

2. The method of claim 1, wherein each of the first signal parameter and the second sound signal are determined over a period of time, and wherein the comparing identifies the sound signal having the lowest noise level over the period of time.

3. The method of claim 1, further comprising:
based on the first noise floor and the second noise floor, determining a first weight for the first sound signal and a second weight for the second sound signal, wherein generating the stimulation signals comprises: (a) based on the first weight, weighing the first sound signal to provide a first weighted signal; (b) based on the second weight, weighing the second sound signal to provide a second weighted signal; (c) providing a combined signal by combining the first weighted signal and the second weighted signal; and (d) based on the combined signal, generating the stimulation signals.

4. The method of claim 3, further comprising:
receiving a third sound signal;
determining a third noise floor indicative of a lowest noise level in the third sound signal;
based on the third signal parameter, determining a third weight for the third sound signal; and
based on the third weight, weighing the third sound signal to provide a third weighted signal, wherein providing the combined signal further comprises combining the first weighted signal, the second weighted signal, and the third weighted signal.

5. The method of claim 1, wherein at least one of the first sound input device or the second sound input device comprises a beamforming microphone.

6. The method of claim 1, wherein at least one of the first sound input device or the second sound input device comprises a wireless microphone.

7. The method of claim 1, wherein the auditory prosthesis system comprises a component of a device configured to generate data specifying the stimulation signals to be generated.

8. The method of claim 1, wherein the auditory prosthesis system comprises a cochlear implant.

9. An auditory prosthesis system comprising:
a first sound input device configured to receive a first sound signal;
a second sound input device configured to receive a second sound signal; and
at least one processor configured to:
determine a first signal parameter that is a noise floor indicative of a lowest noise level in the first sound signal;
determine a second signal parameter that is of a noise floor indicative of a lowest noise level in the second sound signal;
compare the first signal parameter to the second signal parameter to select a sound signal from one of the first sound signal or the second sound signal that has the lowest noise level; and
generate, using the selected sound signal, stimulation signals capable of causing a hearing precept.

10. The auditory prosthesis system of claim 9, wherein each of the first signal parameter and the second signal parameter is determined over a period of time.

11. The auditory prosthesis system of claim 9, wherein the at least one processor is further configured to:
based on the first signal parameter, determine a first weight for the first sound signal;
based on the second signal parameter, determine a second weight for the second sound signal;
determine a combined signal by: weighing the first sound signal using the first weight to provide a first weighted signal, weighing the second sound signal using the second weight to provide a second weighted signal, and combining at least the first weighted signal and the second weighted signal; and
generate the stimulation signals using the combined signal.

12. The auditory prosthesis system of claim 11, wherein the first sound receiving device is configured to receive at least a third sound signal, and wherein the at least one processor is further configured to: determine a third signal parameter representing a noise floor indicative of a lowest noise level in the third sound signal; based on the third signal parameter, determine a third weight; weighing the third sound signal using the third weight to provide a third weighted signal, and to determine the combined signal, combine the first weighted signal, the second weighted signal, and the third weighted signal.

13. The auditory prosthesis system of claim 9, wherein at least one of the first sound input device or the second sound input device comprises a beamforming microphone.

14. The auditory prosthesis system of claim 9, wherein at least one of the first sound input device or the second sound input device is a wireless microphone.

15. The auditory prosthesis system of claim 9, wherein the at least one processor comprises:
a first processor included in the first sound input device, wherein the first processor is configured to determine the first signal parameter and to generate, based on the selected signal, data specifying a first stimulation signal for the auditory prosthesis system based on the selected signal; and
a second processor included in the second sound input device, wherein the second processor is configured to determine the second signal parameter and to generate, based on the selected signal, data specifying a second stimulation signal for the auditory prosthesis system.

16. The auditory prosthesis system of claim 9, wherein the auditory prosthesis system comprises a first auditory prosthesis for a first ear of a recipient and a second auditory prosthesis for a second ear of the recipient.

* * * * *